US012708568B2

(12) United States Patent
Zavalloni

(10) Patent No.: US 12,708,568 B2
(45) Date of Patent: Aug. 18, 2026

(54) METHOD FOR PRODUCING FOLDED UNDERWEAR PADS

(71) Applicant: GDM S.p.A., Bologna (IT)

(72) Inventor: Alessandro Zavalloni, Bologna (IT)

( * ) Notice: Subject to any disclaimer, the term of this patent is extended or adjusted under 35 U.S.C. 154(b) by 0 days.

(21) Appl. No.: 19/206,119

(22) Filed: May 13, 2025

(65) Prior Publication Data

US 2025/0352400 A1 Nov. 20, 2025

(30) Foreign Application Priority Data

May 15, 2024 (IT) ........................ 102024000010966

(51) Int. Cl.
*A61F 13/15* (2006.01)
*A61F 13/496* (2006.01)

(52) U.S. Cl.
CPC ...... *A61F 13/15747* (2013.01); *A61F 13/496* (2013.01)

(58) Field of Classification Search
CPC .............. A61F 13/49011; A61F 13/496; A61F 13/49017; A61F 13/15699; A61F 13/49; A61F 13/15747; B65B 63/02; B65B 67/1277; B65B 25/145; B65B 35/44
See application file for complete search history.

(56) References Cited

U.S. PATENT DOCUMENTS 4,981,480 A * 1/1991 Gaudet ............. A61F 13/49004 2/919
7,399,266 B2 * 7/2008 Aiolfi ..................... B65H 45/16 493/450
7,765,614 B2 * 8/2010 Takino .................. A61F 13/565 2/111
8,545,474 B2 * 10/2013 Schilpp ................. A61F 13/496 604/394
11,786,414 B2 * 10/2023 Okada ............... A61F 13/49014 604/385.01
12,521,285 B2 * 1/2026 Willhaus ........... A61F 13/49011
2010/0292663 A1 * 11/2010 LaVon .............. A61F 13/49019 604/386
2011/0155304 A1 * 6/2011 Sakaguchi ........ A61F 13/15756 156/443
2011/0173796 A1 * 7/2011 Lavon ................. A61F 13/5622 29/428
2011/0178490 A1 * 7/2011 LaVon .................... A61F 13/64 604/385.24
2011/0287919 A1 * 11/2011 Umebayashi ..... A61F 13/15747 493/416
2012/0152436 A1 * 6/2012 Schneider ......... A61F 13/15747 156/66
2013/0165898 A1 * 6/2013 Rhodes ............... A61F 13/5644 604/386

(Continued)

OTHER PUBLICATIONS

Italian Patent and Trademark Office, Search Report, Oct. 18, 2024.

*Primary Examiner* — Dariush Seif
(74) *Attorney, Agent, or Firm* — Themis Law

(57) ABSTRACT

A method for folding pads shaped as pants includes providing a first wing and a second wing of a pad with hook and loop elements, overturning the first and the second wing by 180° on the plane of the pad, and maintaining the first and the second wing in such position until the pad having the shape of pants is closed.

14 Claims, 3 Drawing Sheets

(56) References Cited

U.S. PATENT DOCUMENTS

2015/0209195 A1* 7/2015 Martynus .......... A61F 13/49413 604/385.28
2017/0095378 A1* 4/2017 Sheehan ........... A61F 13/49011
2017/0246046 A1* 8/2017 Paveletzke .............. A61F 13/49
2017/0252230 A1* 9/2017 Mueller .............. A61F 13/4963
2019/0083326 A1* 3/2019 Komatsubara ......... A01K 23/00
2019/0110934 A1* 4/2019 Manabe .................. A61F 13/49
2019/0117471 A1* 4/2019 Brownlee ......... A61F 13/49017
2021/0059871 A1* 3/2021 Obata ............... A61F 13/49007
2021/0145650 A1* 5/2021 Surushe ............ A61F 13/15699
2021/0145660 A1* 5/2021 Surushe ............ A61F 13/49001
2021/0145663 A1* 5/2021 Hayden ................... A61F 13/64
2022/0023110 A1* 1/2022 Schroer, Jr. ....... A61F 13/49058
2022/0054328 A1* 2/2022 Liu ..................... A61F 13/4963
2023/0097138 A1* 3/2023 Sablone .............. A61F 13/4946 604/358
2024/0000633 A1* 1/2024 Raycheck ......... A61F 13/49011
2024/0033140 A1* 2/2024 DeCristofaro ...... A61F 13/5512
2024/0108518 A1* 4/2024 Aochi ..................... A61F 13/56
2025/0352400 A1* 11/2025 Zavalloni .......... A61F 13/15764

* cited by examiner 2
101, 102
101, 102

10
10
100
101
100
C
C
10
200

20
10
10
100
20
101
100
C
C
200

METHOD FOR PRODUCING FOLDED UNDERWEAR PADS

FIELD OF THE INVENTION

The present invention concerns the technical field inherent in the production of pads.

In particular, the invention refers to an innovative method, and relative machine, which allows the pad to be folded in such a way that the latter is packaged once it has assumed the shape of pants.

BACKGROUND OF THE INVENTION

The production of pads has been known for a long time. The pad, as known, serves for the absorption of liquids and is used in both children and adults when the latter suffer from incontinence or similar problems.

The production of the same has been well known for some time and, in this regard, production lines are used in which a continuous web of product intended to form the pads is made to move forward along a processing path defined by rotatable rollers (or wheels as the case may be), in such a way that during the forward motion the web already processed to form the pad (therefore comprising the various layers of material that make it up) is cut and then folded into a U shape (therefore folded wrapped over) for packaging.

For example, previous publications are known in this regard, including for example publication BO2005A000360 of 25 May 2005.

In accordance with this publication, the continuous web is made to move forward along a processing path comprising three mutually counter-rotating rollers. In the production process, the continuous web is cut transversely in such a way as to define the single pad which, then, with the aid of the further two rollers and through the aid of suction systems together with appropriate folding fingers, is folded into a V to obtain a finished product ready for packaging.

A further publication describes a system similar to the previous one, in which, however, there is an oscillating transfer member which is used to facilitate the transfer from one roller to another in the path of processing and folding the product.

The pads thus folded, however, do not maintain their folded condition, i.e. when they are removed from the package are free to reopen into a flat form. In particular, they are simply folded in two halves one on top of the other but they are not stably closed to form pants.

The pads commonly produced have side wings so that they can instead be closed with the shape of pants, maintaining this shape of pants. In particular, a first wing emerges from one flank while a second wing emerges from the opposite flank at one longitudinal end of the pad. The first wing is connected with a third wing in line with it and arranged at the opposite longitudinal end and, in the same way, a fourth wing is in line with the second wing at the opposite longitudinal end.

In some solutions the process is known that allows these pads to be packaged with the wings already connected to each other and, therefore, with the shape of pants so as to be ready for use and to be easily worn.

It is therefore known to produce and consequently package pants of this shape, possibly adjustable through, again, said wings.

More in particular, such wings (therefore said first wing, second wing, third wing and fourth wing) can be equipped with a quick connection system, for example with a hook and loop connection system (called Velcro in the trade), in which the fibers of the Velcro material (generally the fibers relating to the material of which a wing is made) are hooked to the layer having the hooks, with a therefore stable and easily removable connection that allows a quick closure and a quick release.

Then, for example, the first wing and the second wing can provide for the hook system to connect with the fibers relative to the material for making the third wing and the fourth wing.

A technical problem is therefore that of being able to hook together, already in the production step before packaging, these wings provided with a connection system (for example with Velcro) in order to give the pad the shape of pants and therefore to be able to package it already with this shape of pants.

To perform this operation it is necessary to overturn a pair of wings, i.e. for example the first wing 101 and the second wing 101, on the plane 100 of the pad to bring their connection means, for example the hooks of the Velcro, to be able to be connected with the complementary connection means (for example said fibers) present in the other pair of wings, i.e. for example the third wing and the fourth wing.

This overturning is necessary because the connection of the wings, in the pants-like closure, must form a flat strip that surrounds the flank, making sure that the face of the wing in contact with the skin is the one without connection means, in particular without the hooks, for obvious reasons of comfort.

More particularly, therefore, with reference to FIG. 1, the stretched pad 100 shows the surface 100 intended to come into contact with the body together with the faces of the first wing (101), second wing (101), third wing (102) and fourth wing (102) that come into contact with the body.

If, for example, the Velcro system is used, the hooks of the Velcro must be positioned on the face of the wing opposite the plane 100 of the pad (see FIG. 1), in such a way that the connection requires an overturn of the wing 101 (see FIG. 2) and thus ensuring that the wing face that comes into contact with the body during use is the smooth part.

The current known solutions through which this overturning is carried out are not reliable as the wings, along the processing path, are only partially folded and, following this partial folding, are maintained free and fluttering so that the coupling between them to carry out the closure is not precise. It is clear that according to this solution the process is not reliable and it is, therefore, not certain that the correct hooking of a wing can take place in order to couple it with the complementary one, especially when the production speeds are very high and therefore the product travels at high speeds, this increasing the free fluttering of the wings. The faster the product is moved forward, the easier it is for the wings to flutter uncontrollably, preventing intended systems from being able to couple them correctly and being able to perform this operation in a precise and reliable manner.

There is therefore a problem of reliability in the production process of shaping the pad like pants.

SUMMARY OF THE INVENTION

Therefore, it is an object of the present invention to provide a method that solves at least in part the aforementioned technical drawbacks.

In particular, it is the object of the present invention to provide a method that, in the production of pads, allows folding and coupling together the wings with which the pad is provided, in order to close the pad with the shape of pants, the whole with a process that is reliable and precise, even at high production speeds.

These and other objects are obtained with the method for folding a semifinished product (1) of an absorbent product for sanitary use to form a product with the shape of pants (2), according to claim 1.

This method comprises the following steps:

The movement of the semifinished product (1) along a processing path.

For example, as is well known, the processing path can be defined by mutually counter-rotating rollers (or wheels as the case may be) (two or more than two, for example three rollers) which determine the forward motion of the product being processed while this is suitably processed in order to obtain a stretched semifinished product (1) as per FIG. 1 which actually forms the pad before it is folded to form the pants (2).

Preferably, therefore, it is the path of forward motion itself that is movable and that determines the forward motion of the product, for example when the path of forward motion consists of rollers or rotatable wheels.

The semifinished product (1) is therefore actually the pad in stretched position, therefore before it is shaped like pants (2) and therefore the final product to be packaged and placed on the market.

The semifinished product (1) comprises a first wing (101) arranged on one side thereof and at or near a first longitudinal end of the semifinished product (see longitudinal axis A-A of FIG. 1).

The semifinished product also comprises a second wing (101) arranged on an opposite side thereof with respect to said first wing (101) and at or near said first longitudinal end of the semifinished product.

A third wing (102) is then provided arranged on the same side as the first wing (101) and at or near a second longitudinal end of the semifinished product opposite the previous said first end.

A fourth wing (102) is also provided arranged on the same side as the second wing (101) and at or near said second longitudinal end of the semifinished product opposite said first end.

The method provides for moving said semifinished product along a processing path and wherein the method, along this processing path, comprises the following steps:

Folding said first wing (101) and said second wing (101) in such a way as to lift said first wing (101) and said second wing (101) and overturn them on the plane (100) of the semifinished product.

Advantageously, therefore, in this way an overturned position is reached, thus bringing the first quick connection means (or elements) with which said first wing (101) and said second wing (101) are provided to face the outside of the plane (100) of the semifinished product (1).

It therefore follows a step of maintaining said first wing (101) and said second wing (101) in said overturned position.

In this way, advantageously, both the first wing (101) and the second wing (101) are lifted, which are overturned on the plane (100) of the semifinished product (1).

In particular, therefore, the first wing (101) and the second wing (101) that branch externally from the two opposite flanks of the semifinished product (1) are folded to be overturned for resting on the plane (100) of the semifinished product (1) and therefore on the surface of the semifinished product (1).

A step of maintaining in said overturned condition therefore occurs.

In this way, advantageously, with this overturning of the first wing (101) and of the second wing (101), said first wing (101) and second wing (101) are brought to rest on the plane 100 of the semifinished product (1) that in use comes into contact with the body. In this way, the first quick connection means, with which said first wing 101 and the second wing 101 are provided, face the outside of the plane 100 of the semifinished product (see FIG. 2—in essence they face the third wing and the fourth wing for connection).

This overturning and maintaining in an overturned position on the plane 100 means that said first wing 101 and second wing 101 are therefore ready for connection respectively with the complementary third wing (102) and fourth wing (102), at the same time being arranged in a highly stable position and therefore without any action of uncontrolled fluttering.

Said semifinished product (actually the pad still not closed to form the pants) has, in fact, as mentioned, at or near the other second longitudinal end opposite the first end, a third wing (102) arranged on one flank thereof and a fourth wing (102) on the opposite flank.

These third wing and fourth wing (102) are equipped with second quick connection means (or elements) complementary to the previous ones in order to be able to connect to them.

It therefore follows a step of transverse folding said semifinished product 1 closing it wrapped over in such a way that respectively the first wing (101) is led to engage with the third wing (102) and the second wing (101) is led to engage with the fourth wing (102) through said first quick connection means which engage with the complementary second quick connection means with which the third wing (102) and the fourth wing (102) are provided.

The finished product is thus obtained, that is, the pad folded and connected to form the pants.

In this way, all the above-mentioned inconveniences are easily solved.

In particular, thanks to the overturning of the first wing and the second wing on the surface 100 of the semifinished product 1 (or plane 100 as the case may be), by maintaining them in said position, the first quick connection means are exposed which are ready to connect with the second complementary quick connection means present on the third wing and fourth wing.

This overturned position of the first wing and the second wing is maintained until the connection with the third wing and the fourth wing is completed, respectively, following said step of folding the semifinished product 1 transversely.

In addition, maintaining the first wing and the second wing in an overturned position on the surface 100 (or plane 100 as the case may be) of the pad guarantees greater stability of the wings that are prevented from fluttering, making it safer and easier to couple even at high speeds.

In a possible solution, said first quick connection means and the complementary second quick connection means are of the releasable type, so they can be connected to each other, and then possibly separated from each other and possibly reconnected again to each other for as many times as necessary.

In this way, the product is sold and packaged in such a way that it has the shape of the pants but the user can still disconnect said first connection means and said second complementary connection means from one another in order to adjust the pelvis width of the pants, for example.

A preferred solution of the invention provides for the use of the Velcro system.

In particular, for example, said first quick connection means and the complementary second quick connection means may be of the Velcro type.

More particularly, for example, the first connection means provided in the first wing (101) and second wing (101) can provide the Velcro part formed by the hooks and then intended to connect with the fibrous material that constitutes the other Velcro part present on the third wing (102) and fourth wing 102.

In this sense, therefore, the Velcro layer comprising said hooks is connected, for example by means of glue, on the surface of the first wing 101 and second wing 101.

The fibrous complementary layer that couples with the hooks could be connected on the third wing 102 and fourth wing 102.

However, in a preferred configuration of the invention, the material itself of which at least the third wing 102 and the fourth wing 102 are made is generally fibrous such that if, for example, the first connection means present in the first wing 101 and the second wing 101 are the hooks of the Velcro, the second connection means of the third wing 102 and the fourth wing 102 can provide for the fibrous material which does not need to be integrated into said third wing 102 and fourth wing 102 with a special layer, since this fibrous material of said third wing and the fourth wing is already suitable in itself for connection to the hooks.

In this case, therefore, the complementary second connection means are included in the same nature of the material of at least said third wing 102 and fourth wing 102 (for example in non-woven fabric, cotton etc.).

Advantageously, according to an advantageous aspect of the invention, a step of adjusting the width of at least one portion of the semifinished product 1 can be provided in such a way that said folded first wing 101 and second wing (101) are longitudinally aligned with the third wing and the fourth wing (102).

In fact, the folding of the first wing (101) and second wing (101) may require an alignment of the third wing and fourth wing.

In this way, during their coupling, there is certainty of a precise and therefore stable connection.

Advantageously, in a possible solution, said step of adjusting the width may consist of a narrowing of the portion of semifinished product comprising the third wing (102) and the fourth wing (102) in such a way as to draw them reciprocally close to each other by a predetermined amount, thus compensating for the overturn of the first wing and of the second wing.

This narrowing operation can occur in various ways.

For example, it can occur through a specific shape of a rest surface on which the semifinished product is forced to rest, maintaining the semifinished product adhering onto said surface during its movement.

By shaping the surface with a specific geometry, this alignment can be easily made.

Advantageously, in a variant of the invention, said narrowing can occur, for example, through a suction acting on said third wing and the fourth wing (102) and with said suction which, during the forward motion of the semifinished product along its path, moves in such a way as to draw the third wing and the fourth wing close to each other, maintaining them in said close position until coupling with the first wing and the second wing.

For example, translatable blocks 30 (defined in technical jargon as shoes 30) equipped with transverse movement and perforated for the passage of the suction can be used. They are positioned under said third wing and fourth wing and, once suction is activated, they translate thus dragging said third wing and fourth wing to carry out the mutual approach.

Advantageously, said overturn of the first wing (101) and of the second wing (101) on the surface 100 of the semifinished product comprises a step of lifting said first wing (101) and second wing (101) through an airflow and a subsequent folding step which completes overturn thus bringing both said first wing (101) and second wing (101) to complete rotation until reaching a position laid on the plane (100) of said semifinished product.

Advantageously, as also clarified below, the first wing 101 and second wing 101 overturned on the plane 100 are maintained in this position until at least the completion of their connection with the third wing 102 and fourth wing 102, for example by maintaining them in said overturned position through a suction or through suitable mechanical systems.

Advantageously, said overturn of the first wing and the second wing (101) on the plane 100 of the semifinished product can therefore comprise a step of lifting said first wing and second wing through an airflow.

Advantageously, a subsequent folding step can therefore follow, which brings both said first and second wing to complete rotation until reaching said position laid on the plane of the semifinished product.

Advantageously, said folding step that completes overturn of the first wing and second wing can be carried out for example through fixed devices (20).

So, ultimately, a rotation part takes place with a special airflow and the final rotation part can take place through special devices, for example fixed or movable.

For example, in the case of fixed devices, such fixed devices can be arranged in such a way as to intercept the path of forward motion of the semifinished product.

Advantageously, they can have such a shape as to cause said completion of overturn of the first wing and second wing during the forward motion of the semifinished product, bringing said first wing and second wing from the lifted position through the airflows to said position laid on the plane 100 of the semifinished product 1.

As mentioned, maintaining in said laid position the first wing and the second wing can take place for example through suction.

The semifinished product, therefore, moves forward and is intercepted by the fixed devices that complete the overturning. The folded configuration laid on the plane 100 is maintained by the suction while the forward motion of the semifinished product itself frees said first wing and second wing folded by the fixed devices 20.

In an alternative, advantageously, said folding step that completes the overturn of the first wing and second wing can be carried out through movable devices (20), for example translatable and/or transversely movable.

Advantageously, such movable devices can move for example transversely by intercepting said first wing and second wing during the forward motion of the semifinished product and thus bringing said first wing and second wing from the lifted position through the airflows to the position laid on the plane of the semifinished product.

In this case, advantageously, maintaining the first wing and the second wing in said laid position can occur, for example, by maintaining the contact of said movable devices which, therefore, once said first wing and second wing have been intercepted, move integrally with the forward motion of the semifinished product.

Alternatively, they can be pulled back after activating a suction that will maintain said first wing and second wing in an overturned position.

In essence, said movable devices move away from said first wing and second wing, thus releasing them.

Advantageously, in the event that said movable devices maintain the first wing and the second wing in overturned position, said movable devices are pulled back only after the coupling step of said first wing and second wing together with the third wing and fourth wing respectively and therefore after the formation of the pants 2.

Advantageously, in the event that said movable devices maintain the first wing and second wing in overturned position without being pulled back, said movable devices move integrally with said first wing and second wing (101) and are pulled back when the coupling of the first wing and second wing with the third wing and fourth wing respectively has been completed.

In all the aforesaid cases, at the end of the coupling of said wings to each other as described above, a further pressing step can be provided for ensuring a better adhesion of the wings to each other, thus completing the processing of the semifinished product, obtaining the pants 1.

In all the configurations described, it is reminded here that the path of forward motion is movable so that the product being processed is dragged, for example in the case of rotatable wheels.

BRIEF DESCRIPTION OF THE DRAWINGS

Further features and advantages of the present method and relative machinery, according to the invention, will become clearer with the following description of some of its embodiments, made by way of non-limiting example, with reference to the accompanying drawings, in which:

FIG. 1 shows the first wing 101 and the second wing 101 that branch from the flank of the pad and with such first wing and second wing provided with a first Velcro system part in a way such as to be able to couple, each one, with the relative third wing 102 and fourth wing 102 that comprises the second Velcro part; FIG. 2 shows said first wing 101 and second wing 101 folded on the plane 100 of the pad in order to bring the first Velcro system part facing in such a way as to connect with the second Velcro system part present on the third wing 102 and fourth wing 102;

DETAILED DESCRIPTION OF EMBODIMENTS OF THE INVENTION

The present invention is now described in detail with reference to the accompanying figures.

Figure 1:
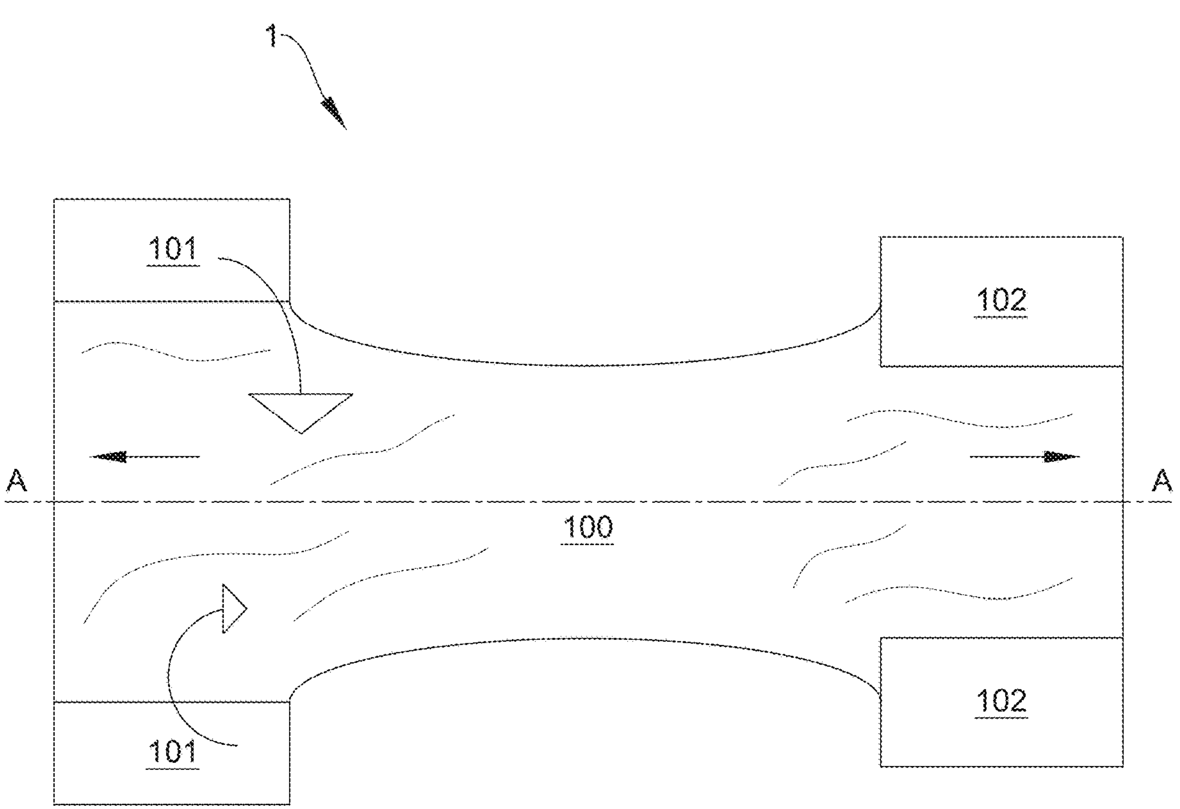
FIGS. 1 and 2 show a pad according to the known art in a stretched (or open, as the case may be) position; in particular.

FIG. 1 shows a schematization of the semifinished product 1 (i.e. the pad 1 before it is closed to form the pants 2, i.e. the finished product to be packaged) well known in the state of the art as already described in the prior art.

Figure 2:
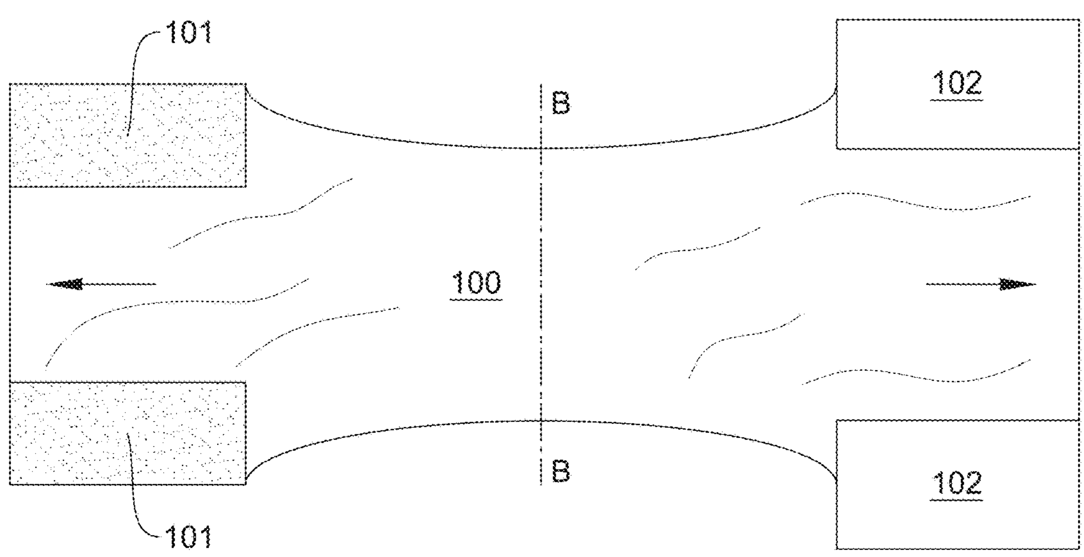
Figures 3, 4, 5:
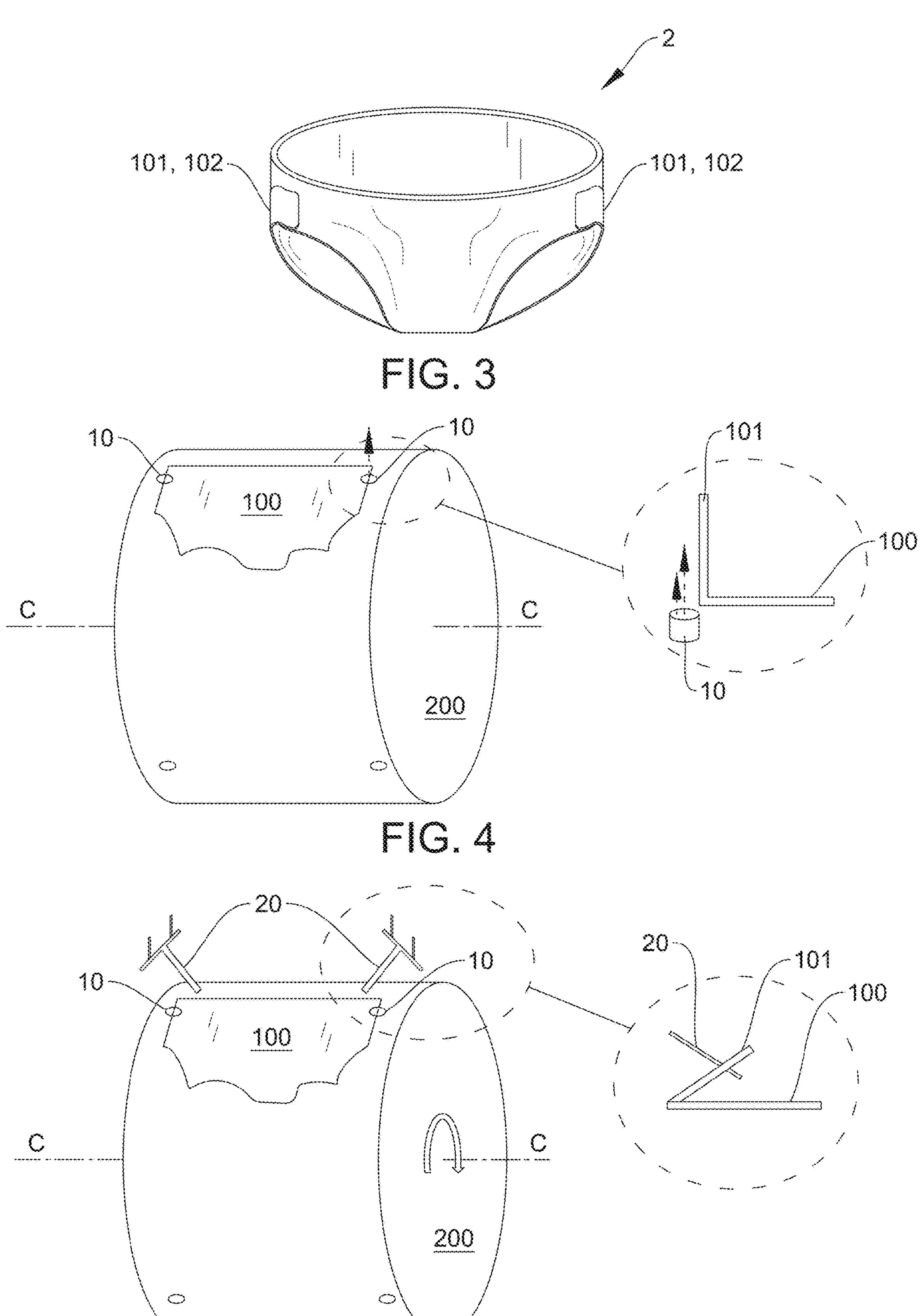
FIG. 3 shows the pad closed with the shape of pants 2 through the Velcro system.
FIG. 4 shows a schematization of the roller 200 on which the pad passes in its processing and folding process and the figure highlights the nozzle 10 which, with an air jet, brings the first wing and the second wing 101 to rise with respect to the plane of the pad.
FIG. 5 shows a possible solution in which special folding devices 20, for example in the form of fixed fingers 20, are arranged to intercept the path of forward motion of said first wing 101 and second wing 101 when lifted at right angles, in order to complete their folding by completing to overturn them and therefore laying them on the plane 100 of the pad, thus completing a rotation at about 180°.

It develops along a longitudinal line A-A and can be folded along the transverse line B-B (see FIG. 2) to form the pants 2 schematized in FIG. 3.

The semifinished product 1 comprises the wings (101, 102) which thus extend radially to the outside of the body.

In particular, a first wing 101 and a second wing 101 are provided which extend from the two flanks of the pad 1 and which are intended to engage with further a third wing 102 and a fourth wing 102 that extend in the same way from the two flanks of the pad. Therefore, with respect to the transverse line B-B of FIG. 2, said first wing 101 and second wing 101 extend from one part of the pad while the other two complementary wings 102, i.e. the third wing 102 and the fourth wing 102, extend from the opposite part of the line B-B.

As mentioned above, the reciprocal connection of a wing 101 with the complementary wing 102 occurs through connection means (generally of a quick type) which provide first connection means adapted to releasably engage with the second complementary connection means (generally of a quick type as mentioned).

In particular, the first wing and the second wing may comprise the first connection means (for example of a quick type) and the third and fourth wing may comprise the complementary second connection means (for example of a quick type) or vice versa.

The pad in top view of FIG. 1 is arranged along a processing line and in a stretched position.

The surface (or plane, as the case may be) 100 shown is the one intended to come into contact with the body of the subject wearing it. FIG. 3 shows when the pad is closed to form the pants 2.

As shown in FIG. 1, the two wings 101 (first wing and second wing) are therefore provided along the longitudinal length of the stretched pad. One of these emerges from one flank and the other, opposed, emerges from the opposite flank. On the opposite part along the longitudinal direction there are the other two complementary wings 102 (i.e. the third wing 102 and the fourth wing 102) always arranged on the two flanks in such a way that the third wing 102 can be coupled with the first wing 101 facing on the same part thereof and the fourth wing 102 can be coupled with the second wing 101 for performing pants-like closure as per FIG. 3.

To perform this operation, as shown in FIG. 1 and as anticipated in the prior art, it is necessary to overturn said first and second wing 101 on the plane 100 of the pad.

This is necessary because the connection of the wings 101-102, in the pants-like closure, must form a flat strip that surrounds the flank, making sure that the face of the wing in contact with the skin is the one without connection means for obvious reasons of comfort.

For this reason, the part of the connection systems arranged in the wings 101 (first wing and second wing), for example the hooks of a Velcro (if Velcro is used), are arranged on the face of the wing 101 facing away from the face that is visible in FIG. 1 (i.e. the face intended for contact with the body). In other words, the hooks of the Velcro are arranged on two opposed wings (for example the first wing 101 and the second wing 101) on the face of both such wings 101 which is opposite the surface 100 of the pad intended to come into contact with the body of the user.

It is therefore necessary, as shown in FIG. 2, to have to overturn said first wing 101 and second wing 101 thus making visible the quick connection systems as per FIG. 2 (for example the hooks of the Velcro as mentioned) which are arranged on said wings 101 and which serve to connect with the fibers of the further third wing and fourth wing 102.

Said third wing and fourth wing 102 must not be overturned as the fibrous material that is coupled with the hooks (in the case of use of Velcro) must be present on the face of the wing 102 facing the outside of the surface 100 (see always FIGS. 1 and 2). This fibrous material can be applied with a special layer or be part of the material itself constituting the wing 102. Upon coupling, the resulting strip in contact with the body is substantially the only face of the wing 101 without the quick connection means.

In a preferred form of invention, said connection means (and therefore the first connection means and the complementary second connection means) may provide for the use of Velcro, whereby having quick-type connection means.

The Velcro system is itself well known and provides for a series of hooks emerging from one surface that are engaged in a series of fibrous elements emerging from another surface. When they are coupled, the hooks of one surface are engaged with the fibrous elements of the opposed surface.

In the proposed solution, therefore, said first wing and second wing 101 can be provided for example with such hooks of the Velcro with the surface relative to the third wing 102 and fourth wing provided with a further surface of fibrous material and/or vice versa.

In this sense, therefore, said first wing and second wing 101 can therefore provide first Velcro quick connection means 101 (for example said hooks or fibrous material) adapted to releasably engage with the second Velcro complementary quick connection means 102 which are obviously the complementary ones of said first Velcro quick connection means 101 mentioned.

In a variant of the invention, however, it is not excluded that the wings can provide first quick connection means and second quick connection means complementary to each other different from Velcro.

As already introduced, in order to have a correct closure of the pad with the shape of pants, it is necessary that the two wings 101 (i.e. the first wing and the second wing) that are at one end of the pad along its longitudinal length (A-A) be overturned on the body of the pad itself according to the arrow direction indicated in FIG. 1. In fact, the first quick connection means present on these two wings 101 are arranged, in FIG. 1, on the face of the wings 101 opposite that visible in FIG. 1. Therefore, for the connection to take place between the first quick connection means and the second quick connection means present on the third wing and fourth wing 102, it is necessary that said first wing 101 and second wing 101 be overturned by 180° on the plane of the pad, exactly as indicated in FIG. 2. FIG. 2 shows in fact with a schematization the visible first quick connection means (for example as said first Velcro quick connection means). The third wing and fourth wing, on the other hand, must not be overturned and are already ready for connection.

Therefore, as already described, the hooks of the Velcro can be arranged (for example by gluing a special layer provided with hooks) on the face of the first wing and second wing 101 opposite the one seen in FIG. 1 in such a way that, following overturn said first wing and second wing 101 on the plane 100 of the pad, said first quick connection means (for example the hooks) are visible, i.e. facing upwards (therefore to the outside of the plane 100 of the pad).

The second complementary quick connection means, in this example case therefore the fibrous material, do not need to be applied to the third wing and fourth wing but they can be part of the same third wing and fourth wing if these are made of a material of fibrous nature.

In all the aforementioned cases, when the pad, along its processing path, is folded along the transverse line B-B and further pressed, this involves an engagement of the first connection means (for example of the quick type) with the complementary second connection means (for example of the quick type), ensuring that the surfaces of the first wing and second wing 101 that face the inside of the annular pants, therefore in contact with the skin, are the smooth surfaces without the connection systems.

That said, therefore, the invention now describes in more detail a folding methodology of said first wing and second wing 101, in such a way as to fold them about by 180° to bring them in any case to stretch above the plane of the pad, thus bringing them from the configuration of FIG. 1 to that of FIG. 2.

The motion takes place by means of a first rotation that brings the wing 101 at an angle of about 90° with respect to the plane 100 which is followed by a second rotation that brings the wing to the position laid on the plane 100 whereby completing a rotation of about 180°.

Therefore, along the processing path, when it is necessary to lift the wing 101 to overturn it on the plane of the pad, this first rotation can take place by means of an airflow.

In particular, the pad travels on a roller that transports it along the processing path towards the folding section where the folding of the pad takes place along the axis B-B.

FIG. 4 shows a roller of this path in which airflows 10 can be provided arranged based on the width of the product being processed and which project an air jet upwards.

The air jet intercepts the wings 101 of each pad during this production step and maintains said first wing 101 and second wing 101 in a lifted position at 90° (i.e. at right angles or substantially at right angles) with respect to the plane 100 of the pad.

The figure shows in an enlarged view a schematization of the nozzle 10 from which the air jet that lifts the wing 101 is projected. FIG. 4 in the enlarged portion shows the arrangement that the wing 101 assumes and which, as mentioned, can be at 90° or at about 90° with respect to the plane 100 of the pad.

Continuing in the structural description of the invention, it is then necessary to be able to complete the overturning by bringing the wing 101 to lie on the plane of the pad 100.

In particular, in a first possible solution, folding devices 20 of the fixed type can be used, for example in the form of fixed folding fingers 20.

In a particularly simple case such folding fingers can be in the form of extensions external to the roller and fixed to an external supporting structure. These extensions are arranged in such a way as to project towards the two flanks of the roller according to an inclination such as to intercept said first wing and second wing folded at 90°, thus causing their further rotation on the plane 100 of the pad during the movement of forward motion of the product which is obtained through rotation of the roller which integrally drags the product with it. These fingers are particularly simple as they are fixed, that is, not provided with any motion but they are simply arranged according to a certain inclination and arrangement such as to intercept the path of forward motion of the product, in particular such as to intercept said first wing and second wing, in order to fold said wings 101 on the plane 100 of the pad.

In other words, the completion of the rotation takes place during the forward motion of the product by means of rotation of the roller that brings said first wing and second wing to intercept, during the forward motion, said fixed devices which can be, as said, fixed fingers.

FIG. 5 schematizes this simple solution with the fingers, or extensions as the case may be, which are fixed and arranged according to a certain inclination that completes folding of the first wing and second wing, bringing them to lie on the plane 100 of the pad.

In order to maintain this laid position at 180°, special air suctions per se already known in the sector can be used to maintain the product adhering to the roller during forward motion.

Then, for example, immediately downstream of the fingers that cause said further overturning by further 90° of said wings 101, a special suction can be activated to maintain said first wing 101 and second wing 101 in the folded position of FIG. 2.

It is already well known the technology that in such processing rollers provides sectors of suction holes that are activated upon reaching a certain angle of rotation such that the roller can be synchronized with such suction holes such that they are activated whenever the portion of product with the wings 101 reaches and/or passes past said folding fingers 20.

In this way, said first wing 101 and second wing 101 are maintained well folded on the product until the step in which, as already known from the previous documentation, the product is folded into two along the transverse line (B-B) to form the pad and therefore with the wings 101 that have been coupled with the complementary wings 102.

Notwithstanding what has been said so far, in a further variant the folding devices 20 can be movable.

For example, similar to what is described in FIG. 5, such folding devices 20, for example always in the form of fingers or extensions in general, can be fixed to a structure external to the roller and can be provided with a motion for example of rotation or roto-translation or simple translation that facilitates the operation of intercepting the wing 101 to fold it on the plane 100.

The folding devices 20 will therefore have a special movement mechanism that moves them in order to intercept said first wing and second wing, thus allowing a more precise folding. The motion can for example be simple translation from the outside to the inside towards the roller, hence with said fingers mounted on a translating support structure.

Once the two wings (i.e. the first wing and the second wing) have been folded on the plane of the pad, the fold can be maintained always through suction as already mentioned above.

In an alternative, the fingers that are movable as they are mounted on a movable support can also follow the forward motion of the product such that the mobility is such that it both determines the fold and then maintains it with the fingers that press said first wing and second wing 101 into place as they move forward along the path. In this case, suction would therefore not be necessary.

In accordance with this solution, of course, the thickness and geometry of the fingers 20 in general must be such as not to interfere with the quick connection means with which the wing 101 is provided precisely so as not to prevent the connection step with the complementary wing 102.

Once the coupling between the wings 101 and 102 has taken place, the fingers 20 can be pulled back disengaging and reposition themselves to resume the cycle with the next incoming product.

In a further variant, the mobility of the fingers as mentioned may be such that it determines the 180° folding of the wing 101 without, however, following it in the path of forward motion, thus requiring the action of suction to maintain the wing resting on the product.

Still in accordance with the invention, an action on the complementary wings 102 (third wing and fourth wing) may also be necessary in order to bring them into a precise position of perfect coupling with said folded first wing and second wing 101 as described above, so that when the pad is folded wrapped over along the transverse axis B-B the coupling is precise.

Figure 6:
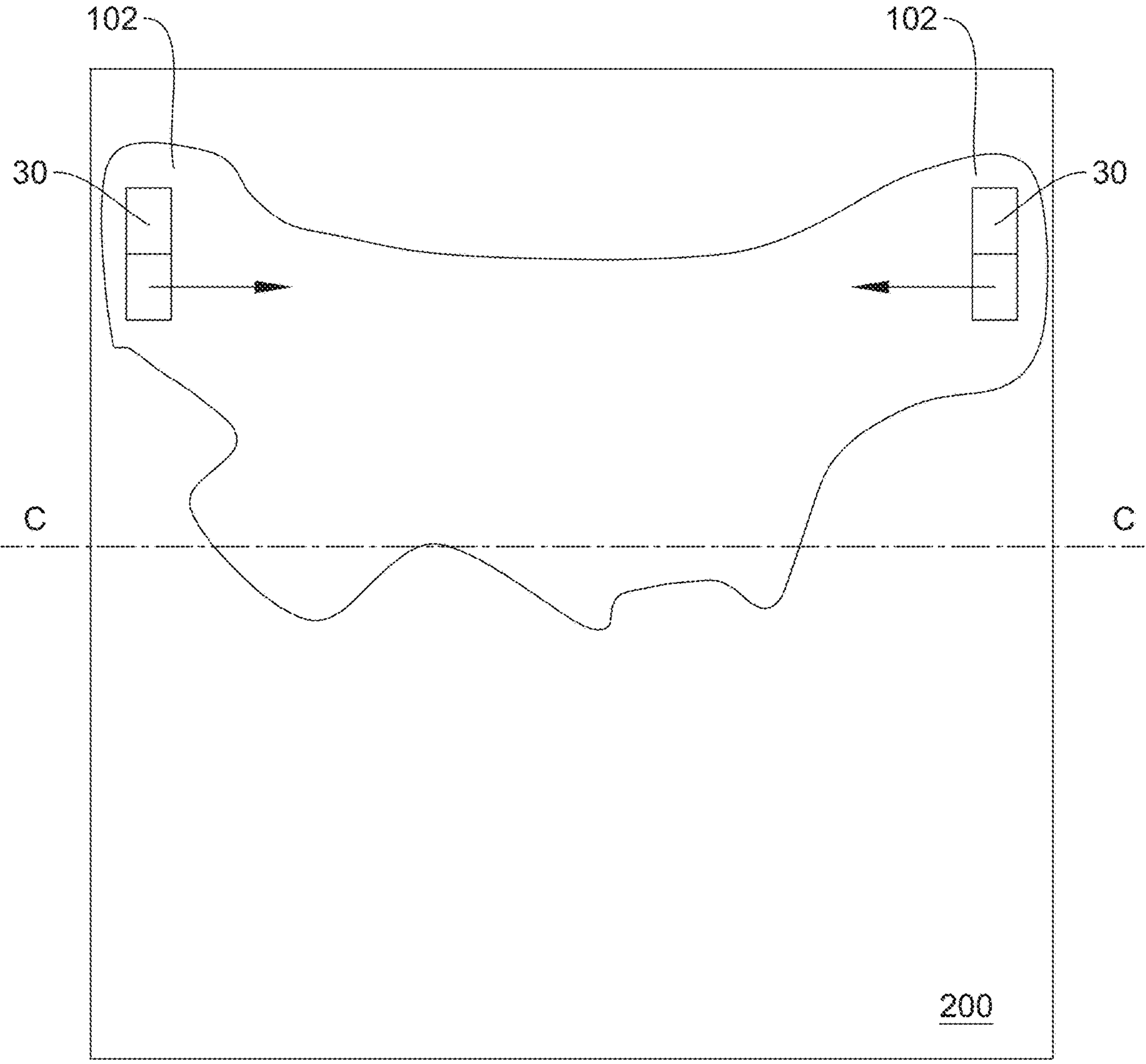
FIG. 6 shows a solution in which two blocks 30 translatable and opposed to each other (said shoes 30 in technical jargon), for example translatable through special guides, integrate in themselves one or more suction nozzles that therefore suck the part of the pad that is positioned above them; specifically, said first wing and second wing are blocked by the nozzles of said shoes; in this way said shoes can be drawn close to each other according to the arrow direction of FIG. 6 so that by making sure that the relative first wing and second wing are drawn close to each other aligning with the third wing and fourth wing; in this way, during the folding step of the pad, said third wing 102 and fourth wing 102 will match perfectly with said folded first wing and second wing 101 laid on the plane 100 of the pad.

In this case, without prejudice to all that has been described so far, the solutions could be as follows:

- in one case there may be blocks 30 (also called shoes 30) applied to the rollers and provided with suction nozzles, with said blocks 30 being translatable transversely on the surface of the roller 200 in such a way as to be able to move on the circumference of the roller from the periphery towards the center and vice versa (See schematization of FIG. 6—axial motion direction C-C).

In particular, the schematization of FIG. 6 shows the two blocks 30 provided with suction nozzles to generate a suction force and thus block said third wing 102 and fourth wing 102. In this way, the suction would act on the wings 102 hence gripping them and the translation of the blocks 30 (see arrow direction) would lead to a translation of the wings 102 by an amount necessary to perfectly superimpose them on the relative first wing 101 and second wing 101. In essence, the blocks 30 could translate along the axis C-C for example moving towards the center, thus bringing the two wings 102 (third wing 102 and fourth wing 102) to be drawn close to each other and thus compensating for the reduction in width of the wings 101 (first wing 101 and second wing 101) due to their folding at 180°, thus leading to a perfect overlap between them.

The translation motion in one direction and then in the opposite direction for the return to the initial position can be obtained in various ways.

For example, in one solution, it would be obtainable via a simple cam system per se widely known in the art. The cams would determine the reciprocal motion (in one direction and therefore also in the opposite direction) as a function of the rotation of the roller. As the roller rotates, a part of the block comes into contact with a cam profile that causes a motion in one direction and as the rotation continues, the cam profile is such as to then determine the motion in the opposite direction to then disengage from the block until the next turn is resumed and so on.

In a variant, the conformation itself of the roller may provide for buckling and/or depressions at specific points that cause the product above arranged to assume a shape such that the wings 101 are then in a position of perfect overlap with the wings 102 when the product is overturned on itself in wrapped over manner.

More specifically, a suction makes the product adhere well and buckling and/or depressions determine collection points that modify the width of the product such that the third wing and the fourth wing will be in line with the first wing and the second wing.

As said the first quick connection means and the second complementary quick connection means may be in the form of Velcro such that the first quick connection means (e.g. the hooks) may for example be placed on the first wing 101 and second wing 101 to releasably couple with the second complementary quick connection means (e.g. the fibers) placed on the opposed third wing 102 and fourth wing 102.

Nothing precludes the use of quick means other than Velcro as an adhesive material.

The invention claimed is:

1. A method for folding a semifinished product of an absorbent product for sanitary use to develop a product having a shape of pants, the semifinished product comprising:

a first wing disposed on a first side and at or adjacently to a first longitudinal end of the semifinished product, a second wing disposed on a second side opposite to the first wing and at or adjacently to the first longitudinal end of the semifinished product, the first wing and the second wing comprising first quick connection elements, a third wing disposed on a same side as the first wing and at or adjacently to a second longitudinal end of the semifinished product opposite to the first end, and a fourth wing disposed on a same side as the second wing and at or adjacently to the second longitudinal end of the semifinished product opposite to the first end, the third wing and the fourth wing comprising second complementary quick connection elements, the method providing for a movement of the semifinished product along a processing path, the method comprising the following steps, along the processing path:

folding the first wing and the second wing so as to lift the first wing and the second wing and overturn the first wing and the second wing on a plane of the semifinished product until reaching an overturned position, thereby causing the first quick connection elements of the first wing and the second wing to face an outside of the plane of the semifinished product;

maintaining the first wing and the second wing in the overturned position; and folding the semifinished product transversally so as to respectively engage the first wing to the third wing and the second wing to the fourth wing by causing the first quick connection elements to engage the second complementary quick connection elements, further comprising a step of adjusting a width of at least one portion of the semifinished product so that the folded first wing and the folded second wing are longitudinally aligned with the third wing and the fourth wing.

2. The method according to claim 1, wherein the first quick connection elements and the second complementary quick connection elements are of hook and loop connections.

3. The method according to claim 1, wherein the step of adjusting the width comprises narrowing a portion of semifinished product comprising the third wing and the fourth wing so as to cause the third wing and the fourth wing to approach each other by a predetermined amount, thus compensating for an overturn of the first wing and of the second wing.

4. The method according to claim 3, wherein the step of narrowing is produced by a specific shape of a rest surface, on which the semifinished product rests, and by causing the semifinished product to adhere onto the rest surface during the movement of the semifinished product.

5. The method according to claim 3, wherein the step of narrowing is produced by a suction acting on the third wing and the fourth wing and by having the suction, during a forward motion of the semifinished product along the processing path, move so as to cause the third wing and the fourth wing to approach each other and to maintain the third wing and the fourth wing in approached position until coupling with the first wing and respectively the second wing.

6. The method according to claim 1, further comprising a pressing after coupling of the first wing, the second wing, the third wing, and respectively the fourth wing together, thereby ensuring a better adhesion of the first wing, the second wing, the third wing, and respectively the fourth wing to each other.

7. A method for folding a semifinished product of an absorbent product for sanitary use to develop a product having a shape of pants, the semifinished product comprising:

a first wing disposed on a first side and at or adjacently to a first longitudinal end of the semifinished product, a second wing disposed on a second side opposite to the first wing and at or adjacently to the first longitudinal end of the semifinished product, the first wing and the second wing comprising first quick connection elements, a third wing disposed on a same side as the first wing and at or adjacently to a second longitudinal end of the semifinished product opposite to the first end, and a fourth wing disposed on a same side as the second wing and at or adjacently to the second longitudinal end of the semifinished product opposite to the first end, the third wing and the fourth wing comprising second complementary quick connection elements, the method providing for a movement of the semifinished product along a processing path, the method comprising the following steps, along the processing path:

folding the first wing and the second wing so as to lift the first wing and the second wing and overturn the first wing and the second wing on a plane of the semifinished product until reaching an overturned position, thereby causing the first quick connection elements of the first wing and the second wing to face an outside of the plane of the semifinished product;

maintaining the first wing and the second wing in the overturned position; and folding the semifinished product transversally so as to respectively engage the first wing to the third wing and the second wing to the fourth wing by causing the first quick connection elements to engage the second complementary quick connection elements, wherein causing the first wing and the second wing to overturn on a surface of the semifinished product comprises:

lifting the first wing and the second wing through an airflow; and a subsequent folding that completes overturning, thereby causing both the first wing and the second wing to complete rotation until reaching a laid position on the plane of the semifinished product.

8. The method according to claim 7, wherein the subsequent folding is carried out with fixed devices that intercept the processing path of forward motion of the semifinished product and that are shaped to cause a completion of an overturn of the first wing and of the second wing during the forward motion of the semifinished product, thereby bringing the first wing and the second wing from a lifted position through the airflow to the laid position laid on the plane of the semifinished product.

9. The method according to claim 8, wherein maintaining the first wing and the second wing in the laid position is performed by suction.

10. The method according to claim 7, wherein the subsequent folding is carried out through transversally movable devices which intercept the processing path of forward motion of the semifinished product so as to cause a completion of an overturn of the first wing and the second wing during the forward motion of the semifinished product, thereby bringing the first wing and the second wing from a lifted position through the airflow to the laid position laid on the plane of the semifinished product, wherein, when the subsequent folding through the transversally movable devices has been completed, the transversally movable devices leave the processing path of forward motion.

11. The method according to claim 7, wherein the subsequent folding step is carried out through movable devices, which, from outside the processing path of forward motion of the semifinished product, move toward the processing path of forward motion of the semifinished product, thereby intercepting the first wing and the second wing and bringing the first wing and the second wing from a lifted position through airflow to the laid position on the plane of the semifinished product.

12. The method according to claim 11, wherein maintaining the first wing and the second wing in the laid position on the plane of the semifinished product is achieved by maintaining contact with the movable devices, which move integrally with the semifinished product under processing or, alternatively, by pulling back the movable devices after activation of suction.

13. The method according to claim 12, wherein, if the movable devices maintain the first wing and second wing in overturned position, the movable devices are pulled back only after coupling the first and the second wing together with the third wing and respectively the fourth wing.

14. The method according to claim 11, wherein, if the movable devices maintain the first wing and the second wing in overturned position without being pulled back, the movable devices move integrally with the first wing and the second wing and are pulled back when the coupling of the first wing and second wing with the third wing and respectively the fourth wing has been completed.

* * * * *